US009907744B2

(12) United States Patent
Massey-Brooker et al.

(10) Patent No.: US 9,907,744 B2
(45) Date of Patent: *Mar. 6, 2018

(54) CONSUMER GOODS PRODUCT COMPRISING LIGNIN OLIGOMER

(71) Applicant: The Procter & Gamble Company, Cincinnati, OH (US)

(72) Inventors: Anju Deepali Massey-Brooker, Newcastle upon Tyne (GB); Mauro Vaccaro, Newcastle upon Tyne (GB); Stefano Scialla, Strombeek-Bever (BE); Bouchra Benjelloun-Mlayah, Pompertuzat (FR); Claudia Crestini, Rome (IT); Heiko Lange, Rome (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/189,005

(22) Filed: Jun. 22, 2016

(65) Prior Publication Data

US 2016/0374935 A1 Dec. 29, 2016

(30) Foreign Application Priority Data

Jun. 24, 2015 (EP) .................................. 15173584

(51) Int. Cl.
| | |
|---|---|
| *A61K 8/97* | (2017.01) |
| *A61Q 5/02* | (2006.01) |
| *A61Q 5/12* | (2006.01) |
| *A61Q 11/00* | (2006.01) |
| *A61K 8/72* | (2006.01) |
| *A61Q 19/00* | (2006.01) |
| *C08H 7/00* | (2011.01) |
| *C09G 1/00* | (2006.01) |
| *C11D 3/382* | (2006.01) |
| *C08L 97/00* | (2006.01) |
| *A61K 8/06* | (2006.01) |
| *A61K 8/73* | (2006.01) |
| *A61Q 19/02* | (2006.01) |
| *C11D 3/00* | (2006.01) |

(52) U.S. Cl.
CPC ............... *A61K 8/97* (2013.01); *A61K 8/06* (2013.01); *A61K 8/72* (2013.01); *A61K 8/736* (2013.01); *A61Q 5/02* (2013.01); *A61Q 5/12* (2013.01); *A61Q 11/00* (2013.01); *A61Q 19/00* (2013.01); *A61Q 19/007* (2013.01); *A61Q 19/02* (2013.01); *C08H 6/00* (2013.01); *C08L 97/005* (2013.01); *C09G 1/00* (2013.01); *C11D 3/0084* (2013.01); *C11D 3/382* (2013.01)

(58) Field of Classification Search
None
See application file for complete search history.

(56) References Cited

U.S. PATENT DOCUMENTS

| | | | |
|---|---|---|---|
| 2,352,021 A | 6/1944 | Schubert et al. | |
| 3,912,706 A | 10/1975 | Rachor et al. | |
| 5,512,276 A * | 4/1996 | Lang ..................... | A61K 8/72 424/401 |
| 6,100,385 A | 8/2000 | Naae et al. | |
| 8,075,637 B2 | 12/2011 | Gizaw et al. | |
| 2003/0139319 A1 | 7/2003 | Scheibel | |
| 2003/0156970 A1 | 8/2003 | Oberkofler et al. | |
| 2008/0125544 A1 | 5/2008 | Yao | |
| 2010/0075878 A1 | 3/2010 | Gizaw et al. | |
| 2011/0114539 A1 | 5/2011 | Stokes et al. | |
| 2013/0233037 A1 | 9/2013 | Adam | |
| 2016/0374921 A1 | 12/2016 | Massey-Brooker et al. | |
| 2016/0374922 A1 | 12/2016 | Massey-Brooker et al. | |
| 2016/0374928 A1 | 12/2016 | Massey-Brooker et al. | |
| 2016/0375138 A1 | 12/2016 | Massey-Brooker et al. | |
| 2016/0376408 A1 | 12/2016 | Massey-Brooker et al. | |

FOREIGN PATENT DOCUMENTS

| | | |
|---|---|---|
| CN | 104 147 977 A | 11/2014 |
| JP | S63 97612 A | 4/1988 |
| JP | H07 215988 A | 8/1995 |
| WO | WO 2010/135804 A1 | 12/2010 |
| WO | WO 2010/135805 A1 | 12/2010 |

(Continued)

OTHER PUBLICATIONS

Pan et al., J. Agric. Food Chem., 2006, vol. 54, pp. 5806-5813.*
Lora, Jairo H., et al., Recent Industrial Application of Lignin: A Sustainable Alternative to Nonrenewable Materials, Journal of Polymers and the Environment, Apr. 2002, pp. 39-48, vol. 10, Nos. 112, XP-002493248.
Pan, Xuejun, et al., Organosolv Ethanol Lignin from Hybrid Poplar as a Radical Scavenger: Relationship between Lignin Structure, Extraction Conditions, and Antioxidant Activity, J. Agric. Food Chem., 2006, pp. 5806-5813, vol. 54, XP008148495.
Ugartondo, Vanessa, et al., Comparative antioxidant and cytotoxic effects of lignins from different sources, Bioresource Technology, 2008, pp. 6683-6687, vol. 99.
Zhang, Jianfeng, et al., Reductive Degradation of Lignin and Model Compounds by Hydrosilanes, ACS Sustainable Chemistry & Engineering, 2014, pp. 1983-1991, vol. 2.

(Continued)

*Primary Examiner* — Brian Gulledge
(74) *Attorney, Agent, or Firm* — John T. Dipre; Steven W. Miller

(57) ABSTRACT

The present invention relates to a consumer goods product comprising a consumer goods product ingredient and a lignin oligomer, wherein the lignin oligomer:
(a) comprises less than 1 wt % sulphur content;
(b) has a number average molecular weight ($\overline{M}_n$) of from 800 Da to 1,800 Da; and
(c) has a molar ratio of aromatic hydroxyl content to aliphatic hydroxyl content in the range of from 1.2 to 1.9, wherein the consumer goods product ingredient is an emulsifier, and wherein the lignin oligomer is in the form of an emulsion, and wherein the consumer goods product is selected from skin treatment composition, oral care treatment composition, and detergent composition.

10 Claims, No Drawings

(56) References Cited

FOREIGN PATENT DOCUMENTS

WO     WO 2014/178911 A1     11/2014

OTHER PUBLICATIONS

Uraki, Yasumitsu, et al., Novel Functions of Non-Ionic, Amphiphilic Lignin Derivatives In: ACS Symposium Series, Jan. 1, 2012, pp. 243-254, American Chemical Society/ Oxford University Press, vol. 1107, Chapter 13, XP055235971.
Extended European Search Report; Application No. 15173599.0-1460; dated Jan. 15, 2016, 9 pages.
Extended European Search Report; Application No. 15173603.0-1460; dated Jan. 15, 2016, 8 pages.
Database GNPD [Online], MINTEL, Mar. 2009, "Eye Contour Cream", XP002751692, Database accession No. 1102156, *the whole document*.
Database GNPD [Online], MINTEL, Apr. 2012, "Aloe Vera Shower Gel", XP002751693, Database accession No. 1765683, *the whole document*.
U.S. Appl. No. 15/189,007, filed Jun. 22, 2016, Massey-Brooker, et al.
U.S. Appl. No. 15/189,009, filed Jun. 22, 2016, Massey-Brooker, et al.
U.S. Appl. No. 15/189,011, filed Jun. 22, 2016, Massey-Brooker, et al.
U.S. Appl. No. 15/189,016, filed Jun. 22, 2016, Massey-Brooker, et al.
U.S. Appl. No. 15/189,019, filed Jun. 22, 2016, Massey-Brooker, et al.

\* cited by examiner

CONSUMER GOODS PRODUCT COMPRISING LIGNIN OLIGOMER

FIELD OF THE INVENTION

The present invention relates to consumer goods products comprising lignin oligomers.

BACKGROUND OF THE INVENTION

Lignins provide anti-oxidant benefits and can act as a surface deposition aid in consumer goods products, such as skin treatment compositions, hair treatment compositions, oral care compositions home care compositions and detergent compositions (especially hand wash detergents). In addition, for home care applications, lignins can also provide surface modification benefits which lead to improved shine and water repellence benefits.

However, lignins are difficult to incorporate in consumer goods products due to their poor solubility in water. In addition, many lignins, such as Kraft lignin, comprise sulphur, which leads to poor chemical compatibility with other ingredients that may be present in consumer goods products, such as transition metals. Sulphur may also cause malodour problems.

The inventors have found that the above problems can be overcome by controlling the level of sulphur content, controlling the number average molecular weight, and controlling the molar ratio of aromatic hydroxyl moiety to aliphatic hydroxyl content.

The inventors have found that specific lignin oligomers can be incorporated into consumer goods products, and give benefits such as anti-oxidation, surface affinity and surface modification benefits without problems such as poor solubility, chemical compatibility and malodour.

SUMMARY OF THE INVENTION

The present invention relates to a consumer goods product comprising a consumer goods product ingredient and a lignin oligomer, wherein the lignin oligomer:
(a) comprises less than 1 wt % sulphur content;
(b) has a number average molecular weight ($\overline{M}_n$) of from 800 Da to 1,800 Da; and
(c) has a molar ratio of aromatic hydroxyl content to aliphatic hydroxyl content in the range of from 1.2 to 1.9, wherein the consumer goods product ingredient is an emulsifier, and wherein the lignin oligomer is in the form of an emulsion, and wherein the consumer goods product is selected from skin treatment composition, oral care treatment composition, and detergent composition.

DETAILED DESCRIPTION OF THE INVENTION

Consumer Goods Product:

The consumer goods product comprises a consumer goods product ingredient and a lignin oligomer. The consumer goods product ingredient and lignin oligomer are described in more detail below.

The consumer goods product may comprise an emollient and/or humectant.

The consumer goods product comprise an emulsifier, this may be preferred when the lignin oligomer is in the form of an emulsion.

The consumer goods product may be a skin treatment composition. The consumer goods product may be an oral care composition.

The consumer goods product may be a detergent composition.

The consumer goods product may comprise chitin and/or chitin derivatives.

The consumer goods product may be selected from: hard surface cleaning sheet and/or wipe; and teeth treatment strip.

The consumer goods product is typically selected from: skin cream; skin lotion; shaving preparation gel or foam; handwash laundry detergent; handwash dishwashing detergent; soap bar; liquid handwash soap; body wash; and toothpaste.

Consumer Goods Product Ingredient: The Consumer Goods Product Comprises an Emulsifier.

Suitable consumer goods product ingredients may include emmolient, humectants, and any combination thereof.

Lignin Oligomer:

The lignin oligomer: (a) comprises less than 1 wt % sulphur content; (b) has a number average molecular weight ($\overline{M}_n$) of from 800 Da to 1,800 Da; and (c) has a molar ratio of aromatic hydroxyl content to aliphatic hydroxyl content in the range of from 1.2 to 1.9.

Preferably, the lignin oligomer comprises from 2.0 mmol/g to 3.0 mmol/g aromatic hydroxyl content.

Preferably, the lignin oligomer comprises from 1.0 mmol/g to 2.0 mmol/g aliphatic hydroxyl content.

Preferably, the lignin oligomer has a weight average molecular weight ($\overline{M}_w$) in the range of from 800 Da to 5,000 Da.

Preferably, the lignin oligomer has a number average molecular weight ($\overline{M}_n$) in the range of from 800 Da to 1,200 Da.

Preferably, the lignin oligomer is essentially free of sulphur.

Preferably, the lignin oligomer has a hydrolysable ester content in the range of from 0.3 mmol/g to 0.7 mmol/g.

Preferably, the lignin oligomer is non-cross linked.

Preferably, the lignin oligomer is derived from corn, sugar cane, wheat and any combination thereof.

Preferably, the lignin oligomer is obtained by an organosolv-like isolation process for the lignins, using preferentially wheat straw, corn stover and/or sugar cane bagasse lignin starting materials.

Preferably, the ratio of aromatic hydroxyl groups to aliphatic hydroxyl groups of the lignin oligomer is within the range of 1.2 to 1.9.

Preferably, the lignin oligomer has a hydrolysable ester content in the range of from 0.2 to 0.5 mmol/g. The hydrolysable ester content preferably comprises acetate and formate functional groups.

Method of Measuring Sulphur Content:

The chemical composition of a lignin sample in terms of its carbon (C), hydrogen (H), nitrogen (N) and sulphur (S) content can be determined by elemental analysis in form of a CHNS analysis of at least three different representative samples of a given batch of the respective lignin. Typical sample sizes are 2.0 mg of a lignin sample that was oven-dried at 105° C. until a steady weight was obtained. The samples are placed in aluminum dishes and analyzed using a Carlo-Erba NA 1500 analyzer, using helium as carrier gas. Carbon (C), hydrogen (H), nitrogen (N) and sulphur (S) were detected in form of carbon dioxide, water, nitrogen, and sulphur dioxide, which are chromatographically separated to exit the instrument in the order of nitrogen, carbon dioxide, water, and sulphur dioxide. Quantification is achieved against calibrations using typical standard substances used for the calibration of elemental analysers, such as (bis(5-tert-butyl-2-benzo-oxazol-2-yl) thiophene, based on the peak areas of the chromatograms obtained for each lignin sample.

Method of Measuring $\overline{M}_n$ and $\overline{M}_w$:

The number average molecular weight, $\overline{M}_n$, as well as the weight average molecular weight, $\overline{M}_w$, can be determined using gel permeation chromatography (GPC). Prior to analysis, representative lignin samples are acetobrominated as reported in archival literature (J. Asikkala, T. Tamminen, D. S. Argyropoulos, J. Agric. Food Chem. 2012, 60, 8968-8973.) to ensure complete solubilisation in tetrahydrofuran (THF). 5 mg lignin is suspended in 1 mL glacial acetic acid/acetyl bromide (9:1 v/v) for 2 h. The solvent is then removed under reduced pressure, and the residue is dissolved in HPLC-grade THF and filtered over a 0.45 μm syringe filter prior to injection into a 20 μL sample loop. Typical analysis set-ups resemble the following specific example: GPC-analyses are performed using a Shimadzu instrument consisting of a controller unit (CBM-20A), a pumping unit (LC 20AT), a degas ser unit (DGU-20A3), a column oven (CTO-20AC), a diode array detector (SPD-M20A), and a refractive index detector (RID-10A); the instrumental set-up is controlled using the Shimadzu Lab-Solution software package (Version 5.42 SP3). Three analytical GPC columns (each 7.5×30 mm) are connected in series for analyses: Agilent PLgel 5 μm 10000 Å, followed by Agilent PLgel 5 μm 1000 Å and Agilent PLgel 5 μm 500 Å. HPLC-grade THF (Chromasolv®, Sigma-Aldrich) is used as eluent (isocratic at 0.75 mL min-1, at 40° C.). Standard calibration is performed with polystyrene standards (Sigma Aldrich, MW range 162-5×106 g mol-1), and lower calibration limits are verified/adjusted by the use of synthesized dimeric and trimeric lignin models. Final analyses of each sample is performed using the intensities of the UV signal at λ=280 nm employing a tailor-made MS Excel-based table calculation, in which the number average molecular weight ($\overline{M}_n$) and the weight average molecular weight ($\overline{M}_w$) is calculated based on the measured absorption (in a.u.) at a given time (min) after corrections for baseline drift and THF-stemming artifacts.

$\overline{M}_n$ is calculated according to the formula $$\overline{M}_n = \frac{\sum w_i}{\sum \frac{w_i}{M_i}}$$

in which $\overline{M}_n$ is the number average molecular weight
$w_i$ is obtained via $$w_i = -i\frac{dV}{d(\log M)}$$

with M being molecular weight
hi being the signal intensity of a given log M measurement point
V being the volume of the curve over a given log M interval d(log M).
$M_i$ is a given molecular weight.

The analysis is run in triplicate, and final values are obtained as the standard average.

$\overline{M}_w$ is calculated according to the formula $$\overline{M}_w = \frac{\sum w_i M_i}{\sum w_i}$$

in which $\overline{M}^w$ is the number average molecular weight
$w_i$ is obtained via $$w_i = -i\frac{dV}{d(\log M)}$$

with M being the molecular weight
hi being the signal intensity of a given log M measurement point
V being the volume of the curve over a given log M interval d(log M).
$M_i$ is a given molecular weight.

The analysis is run in triplicate, and final values are obtained as the standard average.

Eventually necessary adjustment of $\overline{M}_n$ and $\overline{M}_w$ with respect to the desired applications is achieved by mechanical breaking of polymeric lignin using a ball mill, by chemically or enzymatically polymerising oligomeric lignin.

Method of Measuring Aromatic Hydroxyl and Aliphatic Hydroxyl Content:

Typically, a procedure similar to the one originally published can be used (A. Granata, D. S. Argyropoulos, J. Agric. Food Chem. 1995, 43, 1538-1544). A solvent mixture of pyridine and (CDCl3) (1.6:1 v/v) is prepared under anhydrous conditions. The NMR solvent mixture is stored over molecular sieves (4 Å) under an argon atmosphere. Cholesterol is used as internal standard at a concentration of 0.1 mol/L in the aforementioned NMR solvent mixture. 50 mg of Cr(III) acetyl acetonate are added as relaxation agent to this standard solution.

Ca. 30 mg of the lignin are accurately weighed in a volumetric flask and suspended in 400 μL of the above prepared solvent solution. One hundred microliters of the internal standard solution are added, followed by 100 μL of 2-chloro-4,4,5,5-tetramethyl-1,3,2-dioxaphospholane (Cl-TMDP). The flask is tightly closed, and the mixture is stirred for 120 min at ambient temperature. 31P NMR spectra are recorded using suitable equipment, similar or identical to the following example: On a Bruker 300 MHz NMR spectrometer, the probe temperature is set to 20° C. To eliminate NOE effects, the inverse gated decoupling technique is used. Typical spectral parameters for quantitative studies are as follows: 90° pulse width and sweep width of 6600 Hz. The spectra are accumulated with a delay of 15 s between successive pulses. Line broadening of 4 Hz is applied, and a drift correction is performed prior to Fourier transform. Chemical shifts are expressed in parts per million from 85% H3PO4 as an external reference. All chemical shifts reported are relative to the reaction product of water with Cl-TMDP, which has been observed to give a sharp signal in pyridine/CDCl3 at 132.2 ppm. To obtain a good resolution of the spectra, a total of 256 scans are acquired. The maximum standard deviation of the reported data is 0.02 mmol/g, while the maximum standard error is 0.01 mmol/g. (A. Granata, D. S. Argyropoulos, J. Agric. Food Chem. 1995, 43, 1538-1544). Quantification on the basis of the signal areas at the characteristic shift regions (in ppm, as reported in A. Granata, D. S. Argyropoulos, J. Agric. Food Chem. 1995, 43, 1538-1544) is done using a tailor-made table calculation in which the abundances, given in mmol/g, of the different delineable phosphitylated hydroxyl groups are determined on the basis of the integral obtained for the signal of the internal standard, that is present in the analysis sample at a concentration of 0.1 m, creating a signal at the interval ranging from 144.5 ppm to 145.3 ppm. The area underneath the peak related to the internal standard is set to a value of 1.0 during peak integration within the standard processing of the crude NMR data, allowing for determining abundances using simple rule-of-proportion mathematics under consideration of the accurate weight of the sample used for this analysis. The analysis is run in triplicate, and final values are obtained as the standard average.

Method of Measuring Hydrolysable Ester Content:

The total ester content of the lignin can be determined by subjecting the lignin to alkaline hydrolysis conditions: Ca. 500 mg of lignin are dissolved in an excess of 1 M sodium hydroxide solution and heated to temperatures of above 70-80° C. for 12 h. The lignin is subsequently precipitated by acidifying the reaction mixture, isolated and freeze-dried.

Ca. 30 mg of the lignin are accurately weighed in a volumetric flask and suspended in 400 µL of the above prepared solvent solution. One hundred microliters of the internal standard solution are added, followed by 100 µL of 2-chloro-4,4,5,5-tetramethyl-1,3,2-dioxaphospholane (Cl-TMDP). The flask is tightly closed, and the mixture is stirred for 120 min at ambient temperature. $^{31}$P NMR spectra are recorded using suitable equipment under the conditions reported above for the determination of aliphatic and aromatic hydroxyl contents. Quantification of the acid content is done on the basis of the signal intensities at the characteristic shift regions (in ppm) using a tailor-made table calculation referring to the signal of the internal standard. Abundances are typically given in mmol/g. The ester content is obtained as the difference in the abundances of acid groups, aliphatic hydroxyl groups, and aromatic hydroxyl groups found in untreated vs. the lignin treated with sodium hydroxide as outlined above. The analysis is run in triplicate, and final values are obtained as the standard average.

Emollient:

Suitable emollients are silicon based emollients. Silicone-based emollients are organo-silicone based polymers with repeating siloxane (Si 0) units. Silicone-based emollients of the present invention are hydrophobic and exist in a wide range of molecular weights. They include linear, cyclic and crosslinked varieties. Silicone oils are generally chemically inert and usually have a high flash point. Due to their low surface tension, silicone oils are easily spreadable and have high surface activity. Examples of silicon oil include: Cyclomethicones, Dimethicones, Phenyl-modified silicones, Alkyl-modified silicones, Silicones resins, Silica. Other emollients useful in the present invention can be unsaturated esters or fatty esters. Examples of unsaturated esters or fatty esters of the present invention include: Caprylic Capric Triglycerides in combination with Bis-PEG/PPG-1 6/16 PEG/PPG-16/16 Dimethicone and C12-C15 Alkylbenzoate.

The basic reference of the evaluation of surface tension, polarity, viscosity and spreadability of emollient can be found under Dietz, T., Basic properties of cosmetic oils and their relevance to emulsion preparations. SOFW-Journal, July 1999, pages 1-7.

Humectant:

A humectant is a hygroscopic substance used to keep things moist. Typically, it is often a molecule with several hydrophilic groups, most often hydroxyl groups; however, amines and carboxyl groups, sometimes esterified, can be encountered as well (its affinity to form hydrogen bonds with molecules of water is the crucial trait). A humectant typically attracts and retains the moisture in the air nearby via absorption, drawing the water vapour into and/or beneath the organism/object's surface.

Suitable humectants include: Propylene glycol, hexylene glycol, and butylene glycol, Glyceryl triacetate, Neoagarobiose, Sugar alcohols (sugar polyols) such as glycerol, sorbitol, xylitol, maltitol, Polymeric polyols such as polydextrose, Quillaia, Urea, Aloe vera gel, MP diol, Alpha hydroxy acids such as lactic acid, Honey, and Lithium chloride Emulsifier:

An emulsifier generally helps disperse and suspend a discontinuous phase within a continuous phase in an oil-in-water emulsion. A wide variety of conventional emulsifiers are suitable for use herein. Suitable emulsifiers include: hydrophobically-modified cross-linked polyacrylate polymers and copolymers, polyacrylamide polymers and copolymers, and polyacryloyldimethyl taurates. More preferred examples of the emulsifiers include: acrylates/C10-30 alkyl acrylate cross-polymer having tradenames Pemulen™ TR-1, Pemulen™ TR-2 (all available from Lubrizol); acrylates/steareth-20 methacrylate copolymer with tradename ACRYSOL™ 22 (from Rohm and Hass); polyacrylamide with tradename SEPIGEL 305 (from Seppic).

EXAMPLES

Example 1

The following samples were evaluated by the method described below. Sample A is organosolv lignin extracted from Bagasse, Sample B is organosolv lignin extracted from Corn Stover, Sample C is organosolv lignin extracted from wheat straw, Sample D is lignin extracted via steam explosion process (comparative example). Samples A, B and C are the invention examples and Sample D is the comparison example.

TABLE 2

Characteristic data for the example lignins:

| Lignin | Mn [b] (Da) | OH$_{ali.}$ [c] (mmol/g) | OH$_{arom.}$ [c] (mmol/g) | OH$_{arom}$/OH$_{ali.}$ | Sulfur content [a] (%) |
|---|---|---|---|---|---|
| WS-OSL [e] | 1000 | 1.4 | 2.2 | 1.6 | <1 |
| CS-OSL [f] | 1100 | 1.4 | 2.3 | 1.6 | <1 |
| bagasse-OSL [g] | 1100 | 1.6 | 2.4 | 1.5 | <1 |
| ind. SEL [h] | 8000 | 3.2 | 1.3 | 0.4 | <1 |

[a] Determined via elemental analysis (CHNS analysis).
[b] Determined via gel permeation chromatography of acetobrominated samples.
[c] Determined via $^{31}$P NMR spectroscopy of phosphitylated sample..
[e] Industrially produced wheat straw organosolv lignin
[f] Industrially produced corn stover organosolv lignin.
[g] Industrially produced bagasse organosolv lignin.
[h] Industrially produced steam explosion lignin.

Preparation of Turbidity Samples:

Weigh out 0.1 g of lignin and disperse in non-ionic based hard surface cleaning product (Flash diluted in de-ionized water at the recommended dosage of 4.8 ml/l) and stir it for 15 minutes at 200 rpm at room temperature to form a lignin emulsion hard surface cleaning composition. Then, measure the turbidity of the hard surface cleaning composition using the above method with Turbiscan Ageing Station.

Turbidity Data:

| Sample name | % Transmission |
| --- | --- |
| (A) Bagasse | 26.00 |
| (B) Corn Stover | 30.00 |
| (C) Wheat Straw | 54.00 |
| (D) Steam Explosion | 8.50 |

Sample A, B and C in accordance with the present invention showed higher transmission values corresponding to superior solubility properties than the comparison example (Sample D).

Example 2: Illustrative Examples

Hand Dishwashing:

| Examples | Wt % Product I | Wt % Product II |
| --- | --- | --- |
| Alkyl ethoxy sulfate AExS | 16 | 16 |
| Amine oxide | 5.0 | 5.0 |
| C9-11 EO8 | 5 | 5 |
| GLDA | 0.7 | 0.7 |
| Solvent | 1.3 | 1.3 |
| Polypropylene glycol (Mn = 2000) | 0.5 | 0.5 |
| Sodium chloride | 0.8 | 0.8 |
| Lignin | 0.01 | 1.0 |
| Water | Balance | Balance |

Granular Laundry Detergent Compositions Designed for Front-Loading Automatic Washing Machines:

| | Wt % Product I | Wt % Product II |
| --- | --- | --- |
| Linear alkylbenzenesulfonate | 8 | 8 |
| C12-14 Alkylsulfate | 1 | 1 |
| AE7 | 2.2 | 2.2 |
| $C_{10-12}$ Dimethyl hydroxyethylammonium chloride | 0.75 | 0.75 |
| Crystalline layered silicate (δ-$Na_2Si_2O_5$) | 4.1 | 4.1 |
| Zeolite A | 5 | 5 |
| Citric Acid | 3 | 3 |
| Sodium Carbonate | 15 | 15 |
| Silicate 2R ($SiO_2$:$Na_2O$ at ratio 2:1) | 0.08 | 0.08 |
| Soil release agent | 0.75 | 0.75 |
| Acrylic Acid/Maleic Acid Copolymer | 1.1 | 1.1 |
| Carboxymethylcellulose | 0.15 | 0.15 |
| Protease - Purafect ® (84 mg active/g) | 0.2 | 0.2 |
| Amylase - Stainzyme Plus ® (20 mg active/g) | 0.2 | 0.2 |
| Lipase - Lipex ® (18.00 mg active/g) | 0.05 | 0.05 |
| Amylase - Natalase ® (8.65 mg active/g) | 0.1 | 0.1 |
| TAED | 3.6 | 3.6 |
| Percarbonate | 13 | 13 |
| Na salt of Ethylenediamine-N,N'-disuccinic acid, (S,S) isomer (EDDS) | 0.2 | 0.2 |
| Hydroxyethane di phosphonate (HEDP) | 0.2 | 0.2 |
| $MgSO_4$ | 0.42 | 0.42 |
| Perfume | 0.5 | 0.5 |
| Suds suppressor agglomerate | 0.05 | 0.05 |
| Soap | 0.45 | 0.45 |
| Sulphonated zinc phthalocyanine (active) | 0.0007 | 0.0007 |
| S-ACMC | 0.01 | 0.01 |
| Lignin | 0.01 | 1.0 |
| Sulfate/Water & Miscellaneous | Balance | Balance |

Beauty Lotion/Cream:

| | Wt % Product I | Wt % Product II |
| --- | --- | --- |
| Water | Balance | Balance |
| Glycerin | 7 | 7 |
| Disodium EDTA | 0.05 | 0.05 |
| Methylparaben | 0.1 | 0.1 |
| Sodium Dehydroacetate | 0.5 | 0.5 |
| Benzyl alcohol | 0.25 | 0.25 |
| GLW75CAP-MP (75% aq. TiO2 dispersion)[1] | 0.5 | 0.5 |
| Palmitoyl-dipeptide[2] | 0.0001 | 0.0001 |
| N-acetyl glucosamine | 2 | 2 |
| Salicylic Acid | 1.5 | 1.5 |
| Isohexadecane | 3 | 3 |
| PPG15 Stearyl Ether | 4 | 4 |
| Isopropyl Isostearate | 1.3 | 1.3 |
| Sucrose polyester | 0.7 | 0.7 |
| Phytosterol | 0.5 | 0.5 |
| Cetyl alcohol | 0.4 | 0.4 |
| Stearyl alcohol | 0.5 | 0.5 |
| Behenyl alcohol | 0.4 | 0.4 |
| PEG-100 stearate | 0.1 | 0.1 |
| Cetearyl glucoside | 0.1 | 0.1 |
| Polyacrylamide/C13-14 isoparaffin/laureth-7 | 2 | 2 |
| Dimethicone/dimethiconol | 2 | 2 |
| Polymethylsilsequioxane | 0.25 | 0.25 |
| Lignin | 0.01 | 1.00 |

Personal Care Product Containing Skin Lightening:

| Component | Wt % Product I | Wt % Product II |
| --- | --- | --- |
| Disodium EDTA | 0.100 | 0.100 |
| Phlorogine BG | 2.000 | 0 |
| deoxyArbutin | 0 | 2.000 |
| Niacinamide | 5.000 | 5.000 |
| Isohexadecane | 3.000 | 3.000 |
| Isopropyl isostearate | 1.330 | 1.330 |
| Sucrose polycottonseedate | 0.670 | 0.670 |
| Polymethylsilsequioxane | 0.250 | 0.250 |
| Cetearyl glucoside + cetearyl alcohol | 0.200 | 0.200 |
| Behenyl alcohol | 0.400 | 0.400 |
| Ethylparaben | 0.200 | 0.200 |
| Propylparaben | 0.100 | 0.100 |
| Cetyl alcohol | 0.320 | 0.320 |
| Stearyl alcohol | 0.480 | 0.480 |
| Tocopheryl acetate | 0.500 | 0.500 |
| PEG-100 stearate | 0.100 | 0.100 |
| Glycerin | 7.000 | 7.000 |
| Titanium dioxide | 0.604 | 0.604 |
| Polyacrylamide + C13-14 isoparaffin + laureth-7 | 2.000 | 2.000 |
| Panthenol | 1.000 | 1.000 |
| Benzyl alcohol | 0.400 | 0.400 |

-continued

| Component | Wt % Product I | Wt % Product II |
|---|---|---|
| Dimethicone + dimethiconol | 2.000 | 2.000 |
| Lignin | 0.010 | 1.000 |
| Water (to 100 g) | Balance | Balance |

Automatic Dishwashing Cleaning Composition:

| | Powder (wt % based on 19 g portion) | Powder (wt % based on 19 g portion) |
|---|---|---|
| STPP | 34-38 | 34-38 |
| Alcosperse[1] | 7-12 | 7-12 |
| SLF-18 Polytergent[2] | 1-2 | 1-2 |
| Esterified substituted benzene sulfonate[3] | 0.1-6.0 | 0.1-6.0 |
| Polymer[4] | 0.2-6.0 | 0.2-6.0 |
| Sodium perborate monohydrate | 2-6 | 2-6 |
| Carbonate | 20-30 | 20-30 |
| 2.0r silicate | 5-9 | 5-9 |
| Sodium disilicate | 0-3 | 0-3 |
| Enzyme system[5] | 0.1-5.0 | 0.1-5.0 |
| Pentaamine cobalt(III)chloride dichloride salt | 10-15 | 10-15 |
| TAED | 0-3 | 0-3 |
| Perfume, dyes, water and other components | Balance to 100% | Balance to 100% |

| | Liquid (wt % based on 1.9 g portion) | Liquid (wt % based on 1.9 g portion) |
|---|---|---|
| Dipropylene Glycol | 35-45 | 35-45 |
| SLF-19 Polytergent[2] | 40-50 | 40-50 |
| Neodol ® C11EO9 | 1-3 | 1-3 |
| Lignin | 0.01 | 1.0 |
| Dyes, water and other components | Balance | Balance |

[1] such as Alcosperse ® 246 or 247, a sulfonated copolymer of acrylic acid from Alco Chemical Co.
[2] linear alcohol ethoxylate from Olin Corporation
[3] such as those described above
[4] a sulfonated polymer such as those described above
[5] one or more enzymes such as protease, mannaway, natalase, lipase and mixture thereof.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A consumer goods product comprising a consumer goods product ingredient and a lignin oligomer, wherein the lignin oligomer:
   (a) comprises less than about 1 wt % sulphur content;
   (b) has a number average molecular weight ($\overline{M}_n$) of from about 800 Da to about 1,800 Da; and
   (c) has a molar ratio of aromatic hydroxyl content to aliphatic hydroxyl content in the range of from about 1.2 to about 1.9,
   wherein the consumer goods product ingredient is an emulsifier, and wherein the lignin oligomer is in the form of an emulsion,
   and wherein the consumer goods product is a detergent composition.

2. A consumer goods product according to claim 1, wherein the lignin oligomer comprises from about 2.0 mmol/g to about 3.0 mmol/g aromatic hydroxyl content.

3. A consumer goods product according to claim 1, wherein the lignin oligomer comprises from about 1.0 mmol/g to about 2.0 mmol/g aliphatic hydroxyl content.

4. A consumer goods product according to claim 1, wherein the lignin oligomer has a weight average molecular weight ($\overline{M}_w$) in the range of from about 800 Da to about 5,000 Da.

5. A consumer goods product according to claim 1, wherein the lignin oligomer has a number average molecular weight ($\overline{M}_n$) in the range of from about 800 Da to about 1,200 Da.

6. A consumer goods product according to claim 1, wherein the lignin oligomer has a hydrolys able ester content in the range of from about 0.3 mmol/g to about 0.7 mmol/g.

7. A consumer goods product according to claim 1, wherein the lignin oligomer is non-cross linked.

8. A consumer goods product according to claim 1, wherein the lignin oligomer is derived from corn, sugar cane, wheat and any combination thereof.

9. A consumer goods product according to claim 1, wherein the consumer goods product comprises an emollient and/or humectant.

10. A consumer goods product according to claim 1, wherein the consumer goods product comprises chitin and/or chitin derivatives.

* * * * *